United States Patent
Sun et al.

(10) Patent No.: US 10,054,561 B2
(45) Date of Patent: Aug. 21, 2018

(54) DEVICE FOR DETECTION OF IONIC CONDUCTIVITY AND ITS APPLIED MEASUREMENT

(71) Applicant: DALIAN INSTITUTE OF CHEMICAL PHYSICS, CHINESE ACADEMY OF SCIENCES, Dalian (CN)

(72) Inventors: Gongquan Sun, Dalian (CN); Zhangxun Xia, Dalian (CN); Suli Wang, Dalian (CN); Xudong Fu, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 130 days.

(21) Appl. No.: 15/322,138

(22) PCT Filed: Dec. 14, 2015

(86) PCT No.: PCT/CN2015/097224
§ 371 (c)(1),
(2) Date: Dec. 26, 2016

(87) PCT Pub. No.: WO2016/095769
PCT Pub. Date: Jun. 23, 2016

(65) Prior Publication Data
US 2017/0153196 A1    Jun. 1, 2017

(30) Foreign Application Priority Data

Dec. 19, 2014  (CN) .......................... 2014 1 0811333
Dec. 9, 2015   (CN) .......................... 2015 1 0902821

(51) Int. Cl.
*G01N 27/04*  (2006.01)
*G01N 27/06*  (2006.01)
(Continued)

(52) U.S. Cl.
CPC ............ *G01N 27/04* (2013.01); *G01N 27/06* (2013.01); *G01N 27/4162* (2013.01);
(Continued)

(58) Field of Classification Search
CPC ........ G01N 27/00; G01N 27/02; G01N 27/04; G01N 27/06; G01N 27/26; G01N 27/27;
(Continued)

(56) References Cited

U.S. PATENT DOCUMENTS 4,015,199 A    3/1977  Rommel
6,819,309 B1 * 11/2004 Kishi .................... G02F 1/1333
345/107
(Continued)

FOREIGN PATENT DOCUMENTS

CN    101101271 A    1/2008
CN    101413972 A    4/2009
(Continued)

*Primary Examiner* — Hoai-An D Nguyen
(74) *Attorney, Agent, or Firm* — Enshan Hong; VLP Law Group LLP

(57) ABSTRACT

An ionic conductance measuring instrument comprising a voltage/current test device and a test electrode, in which the test electrode comprises a bulk substrate with four linearly arranged through holes, four Pt wires inserted in the through holes respectively with their upper ends exposed outside of the bulk and their downside ends hidden inside of the bulk; the four axis of the Pt wire is in the same plane and parallel with each other; the gap distance between the mentioned Pt wire and the bulk substrate is 0.1-2 mm, and is filled with ionic conductive polymer.

19 Claims, 3 Drawing Sheets

(51) Int. Cl.
  *G01N 27/416* (2006.01)
  *G01N 27/26* (2006.01)
  *G01R 31/36* (2006.01)

(52) U.S. Cl.
  CPC ........... *G01N 27/26* (2013.01); *G01N 27/416* (2013.01); *G01R 31/36* (2013.01)

(58) Field of Classification Search
  CPC .. G01N 27/416; G01N 27/4162; G01R 31/00; G01R 31/36
  USPC .............. 324/425, 439; 204/193, 194, 228.1, 204/228.6; 436/149, 150, 151, 153, 154
  See application file for complete search history.

(56) References Cited

U.S. PATENT DOCUMENTS

| | | | |
|---|---|---|---|
| 9,929,428 B2* | 3/2018 | Yokoyama | H01M 10/052 |
| 2011/0133676 A1* | 6/2011 | Ikushima | F03G 7/005 |
| | | | 318/116 |
| 2016/0072071 A1* | 3/2016 | Yumura | H01L 51/0047 |
| | | | 320/101 |

FOREIGN PATENT DOCUMENTS

| | | |
|---|---|---|
| CN | 202512173 U | 10/2012 |
| CN | 203011879 U | 6/2013 |

* cited by examiner

DEVICE FOR DETECTION OF IONIC CONDUCTIVITY AND ITS APPLIED MEASUREMENT

RELATED APPLICATIONS

This is a U.S. national stage of international application No. PCT/CN2015/097224 filed on Dec. 14, 2015, which claims priority from China Patent Application No. 201410811333.2 filed on Dec. 19, 2014 and China Patent Application No. 201510902821.9 filed on Dec. 9, 2015, the entire content of these priority applications is incorporated herein as reference.

TECHNICAL FIELD

This invention relates to a method and its apparatus for testing ionic conductivity. Particularly, it is a method for testing ionic conductivity from an electronic conductive material.

BACKGROUND TECHNIQUE

Electronic and ionic conductivity are one of the most important phenomena in the fields of energy materials, sensor devices, biological systems and so on. It is not only important for the efficiency of charge transport, but also relates to the chemical and electrochemical reaction mechanism and rates within the systems. At the meantime, it is also one of the determinative factors for the construction of electrochemical boundaries, and then dominates the performance, cost, and durability of the applied devices. In the fields of advanced energy technologies, including fuel cells, metal-air batteries and lithium ion batteries, the synergy of electron and ion transport is the key factor limiting the development. Therefore, efficient detection of ionic conductivity and electronic conductivity, as well as effective analysis of charge transport channels, is one of the key technologies for synthesis of electrode materials and structures.

The traditional measurements of electronic and ionic conductivity include the two-electrode and four-electrode ohms or electrochemical methods. With years of development, these techniques have been evolved as mature detection systems, and gained success in theoretical and applied aspects. However, in the current electrochemical systems including fuel cells, lithium ion batteries, and electrochemical sensors, the functions of electronic and ionic conductance usually exist synchronously in the microstructure of the electrode in the form of compound channels to ensure the high efficiency and utilization of the electrochemical boundaries and active components. Therefore, in the systems integrated with both the electronic and ion conductivity, it was found difficult to separate ionic conductance from the complicated series and parallel connections of electronic and ionic conductors with the traditional measurement equipped with metal probes. Specifically, the electronic conductivity of the electrode is usually greater than 1 S/cm, generally up to $10\text{-}10^3$ S/cm, much higher than the ionic conductivity in the magnitude order of $10^{-3}\text{-}10^{-1}$ S/cm range. Conventional conductivity testing methods could hide signals of the ion conductance, and then render it impossible to separate efficiently. For this reason, finding a way to effectively separate the electronic conductance from the ionic conductance is critical to the development of advanced materials. On the other hand, the traditional ionic conductance detections are usually performed in the aqueous solution, which obviously differ from the applied environment in the electrode system and hardly reflect the convincible property of the ionic conductance. Therefore, the design and preparation of an conductivity testing instrument with controllable temperature and humidity could lay the foundation of analytical techniques for the development of electrode materials.

SUMMARY OF THE INVENTION

To aim at the deficiencies of the prior art, this invention has been devised as an ion conductive polymer modified four-probe detection apparatus to separate ion-/electron-conductance from the composite conductive materials. This detection apparatus includes an ion-conductive polymer modified probe and the ambient temperature and humidity controlling system, effectively solving the difficulty of the ion-/electron-conductance separation and the problem of environmental differences between measurement and applied status. This invention could accurately detect ionic conductance from the composite conductor materials, with precisely controlled temperature/humidity, increased reproducibility, simplified testing procedures, and enhanced measurement efficiency.

The invention adopts the following specific schemes:

An ionic conductance measuring device is comprising a voltage/current detection part and a test electrode; the test electrode is consisted of a block of substrate, four linearly arranged through holes on the substrate, four platinum wires inserted in the holes with the upper tips extended outside the block and the opposite tips withdrawn inside the block. The axes of the mentioned Pt wire are parallelly aligned in the same plane. The distance between the lower end surface of the platinum wires and the bottom surface of the block substrate is 0.1-2 mm. The gaps between the bottom ends of the Pt wires and the substrate are filled with the ion conductive polymer.

The voltage/current testing device is one of a potentiostat, ohmmeter, ammeter, constant voltage power supply, and a constant current meter.

The distance between the adjacent Pt wires is equal, and the diameters of the Pt wires are equal.

The substrate material is one of polytetrafluoroethylene, polyether ether ketone and polyethylene;

The ion conductive polymer is one of perfluorosulfonic acid polymer, sulfonated polyetheretherketone, quaternized polysulfone, and polybenzimidazole. Such polymers usually have the capability of ionic conductance or could perform ion migration under certain conditions;

The range of the measurement for ionic conductivity is 0.01 to 1000 Ω·cm. The range with minimized error is 0.05 to 100 Ω·cm;

The testing device also comprises a temperature/humidity controllable test box, which includes three airtight chambers: a dry gas chamber, a wet gas chamber and a testing chamber; To adopt the separated dry/wet gas chambers could effectively control the testing humidity without a humidity sensor and simplify the testing system;

The probes of the voltage/current testing device and the testing electrode are arranged in the testing chamber;

A gas inlet-A and a dry gas outlet are fixed on the dry gas chamber, and the inside of the dry gas chamber is filled with dehydration material; a gas inlet-B and a moist gas outlet are fixed on the wet gas chamber, and the deionized water is contained in chamber; The gas outlets of the dry and wet gas are connected to the testing chamber by tubes, and the inlets are connected to an gas supply source by gas flow meters.

The dry gas outlet and the wet gas outlet are connected with the test chamber pipeline through the three-way valve, and the three ports of the three-way valve are respectively connected with the testing chamber, the dry gas outlet and the wet gas outlet; the gas flow meters are one of the rotor flow rate meters, electromagnetic flow meters, and differential pressure flow meters.

The bottom of the test chamber is set with a water outlet, and the water outlet is set with a valve, and the water outlet can be opened or closed, and the water outlet can be opened to discharge liquid water in the test chamber.

The test chamber is provided with a sample test table, and the sample test table is drilled with several through holes, which can drain the liquid water to the bottom of the testing chamber. The upper side of the test chamber is provided with a switchable sample taking-out port.

The humidity controllable testing box is provided with a heat keeping device outside, and the dry gas chamber, wet gas chamber and testing chamber are all covered by the heat keeping device.

The temperature controlling and keeping device is one of a thermostatic water bath and a electric heating jacket.

The dry gas chamber, the wet gas chamber and the testing chamber are made of moisture resistant and heat resistant materials, and the moisture resistant and heat resistant material is one of organic glasses, polytetrafluoroethylene and stainless steel.

The method for measuring ionic conductivity using the testing device involves the followed steps:

(1) measuring the ionic conductance: a sliced thin piece of the testing sample is tightly pressed on bottom end of the testing electrode block; the second and third Pt wires in the test electrode are connected with the potential control terminal, and the first and forth Pt wires are connected with the current control terminal; a certain voltage is applied on the voltage testing terminal, and the response current is recorded; the same procedure is repeated at least twice;

(2) Data processing: the measured current is set as the abscissa, and the voltage is set as the ordinate. A plot of current-voltage is obtained, and the linear section near the zero potential part could be fitted. The slope d of the fitted curve is the ionic resistance of the sample to be measured;

The ionic resistivity $\rho$ of the test sample can be calculated by $\rho=Cd$, where C is the correction factor and can be calculated as follow:

$$C=2\pi/[1/S_1+1/S_2-1/(S_1+S_2)-1/(S_2+S_3)]$$

Where $S_1$, $S_2$ and $S_3$ are the distance between the first Pt wire and the second Pt wire, the second Pt wire and the third Pt wire, the third Pt wire and the fourth Pt wire, respectively. And the conductivity of the sample to be measured is $1/\rho$.

The applied voltage range in step (1) is −1V to 1V.

When the length of the test sample on the vertical scale to the Pt wires is more than 10 times of the distance between the Pt wires, it could be considered to meet the semi-infinite boundary condition, and the conductivity value can be calculated directly from the above equation.

When the ratio of the sample thickness and the distance between the Pt wires is less than 0.5, a correction curve is required by testing a series of samples to evaluate the relationships between the sample thickness and the testing positions.

The ionic conductivity test method can be used to measure the ionic conductivity of samples as carbon paper, carbon powder, carbon fiber, semiconductor, metal, or polymers.

The flow ratio $Q_A:Q_B$ is equal to $X:(1-X)$, where X is the preset humidity, $0 \le X \le 100\%$; and the flow rate ratio of the gas inlet A and the gas inlet B is simultaneously introduced;

The gas is one of nitrogen, argon, air, and oxygen.

The invention solves the problem that the ionic conductivity mixed in the electronic conductor is difficult to measure in the prior art. By adopting this method, the ionic conductance of the electronic conductors could be precisely measured and the ion migration of the materials could also be investigated. This measurement possesses the multi advantages of testing accuracy, stability of temperature and humidity, data reproducibility, simplified procedures and enhanced testing efficiency.

DETAILED DESCRIPTION

Example 1

Figure 1:
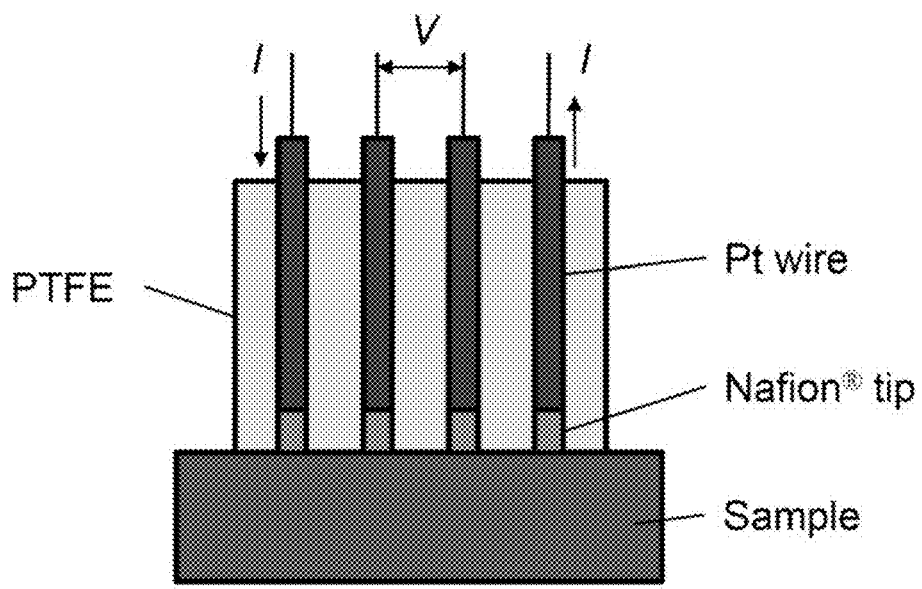
FIG. 1. Schematic of the invention for the measurement of ionic conductivity; in this figure, 1. The insulative block; 2. The Pt wires; 3. The ion conductive polymer; 4. The test sample; 5. The voltage applying terminals; 6. The current response terminals.
Figure 4:
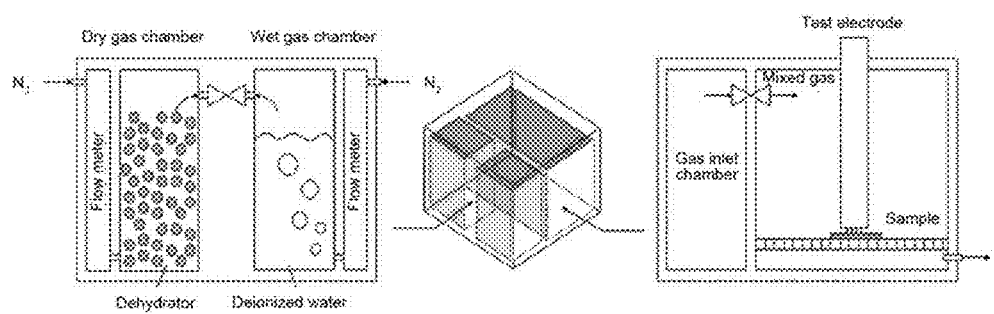
FIG. 4: Schematic of the humidity-controlled test box.

As shown in FIGS. 1 and 4 of the schematic of the test device, the cylindrical PTFE block with diameter of 2 cm is drilled along the axis out four linear through-holes with the diameter of 1 mm and the adjacent distance of 3 mm. Four Pt wires of the same diameters as the holes were fixed in the holes, and the end surface of the Pt wires was 1 mm from the end surface of the PTFE block. The 5% Nafion ionomer solution was applied dropwise onto the end surfaces of the Pt wires. After drying, the coating was repeatedly applied until the Nafion polymer solid completely covered the end surfaces of the Pt wires.

Figure 2:
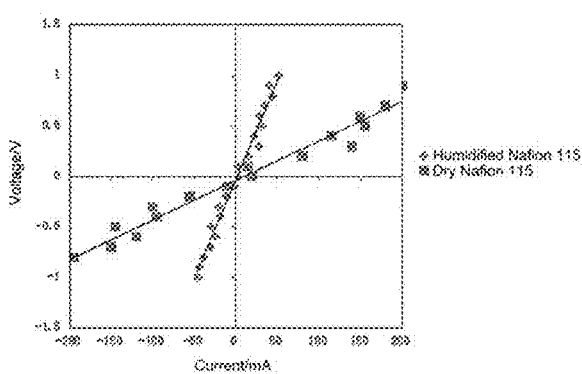
FIG. 2: Test results for Example 1 and Example 2.
Figure 3:
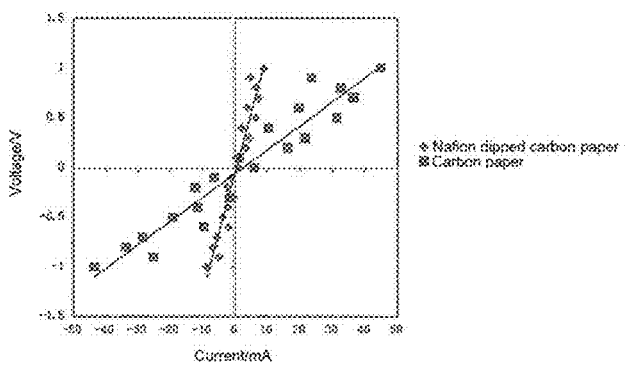
FIG. 3: Test results for Example 3 and Example 4.

The middle two Pt wires of the test circuit are connected to the voltage test terminals (reference electrode 1 and 2) of the potentiometer, and the outer two Pt wires are connected to the current test terminal (working electrode and counter electrode).

a. Measurement of Ionic Conductance:

A dried Nafion 115 film with a size of 5×5 $cm^2$ is closely contacted with the Nafion ionomer modified end of the test electrode. The potential signals were applied to the voltage test terminals with a voltage range of −1 to 1 V, and the current response signals were then recorded at the current test terminals.

b. Data Processing:

The above measured current data are set as the abscissa, and the voltage data are set as the ordinate, and an approximate linear curve could be obtained as shown in FIG. 2. The linear fitting of the curve near the zero potential is performed, and the slope d of the fitting curve is the test ion resistance of the sample.

The ionic resistivity of the material is corrected by $\rho=Cd$, and C is the correction factor. When the spacing S between the probes is equal, $$C=2\pi S$$

The measured ionic conductivity of the non-humidified Nafion 115 membrane is about 0.026±0.004 S cm$^{-1}$.

Comparative Example 1

The experiment is carried out by the unmodified four-probe method. The cylindrical PTFE block with diameter of 2 cm is drilled along the axis out four linear through-holes with the diameter of 1 mm and the adjacent distance of 3 mm. Four Pt wires of the same diameters as the holes were fixed in the holes, and the end surface of the Pt wires was 0.5 mm reaching out from the end surface of the PTFE block.

The middle two Pt wires of the test circuit are connected to the voltage test terminals (reference electrode 1 and 2) of the potentiometer, and the outer two Pt wires are connected to the current test terminal (working electrode and counter electrode).

a. Measurement of Ionic Conductance:

A dried Nafion 115 film with a size of 5×5 cm$^2$ is closely contacted with the Nafion ionomer modified end of the test electrode. The potential signals were applied to the voltage test terminals with a voltage range of −1 to 1 V, and the current response signals were then recorded at the current test terminals.

b. Data Processing:

The above measured current data are set as the abscissa, and the voltage data are set as the ordinate, and an approximate linear curve could be obtained. The linear fitting of the curve near the zero potential is performed, and the slope d of the fitting curve is the test ion resistance of the sample.

The ionic resistivity of the material is corrected by $\rho = Cd$, and C is the correction factor. When the spacing S between the probes is equal, $$C = 2\pi S$$

The measured ionic conductivity of the non-humidified Nafion 115 membrane is about 0.030±0.003 S cm$^{-1}$. This result is similar to that of the Example 1, and indicates the convincing test results of the measurement.

Example 2

As shown in FIGS. 1 and 4 of the schematic of the test device, the cylindrical PTFE block with diameter of 2 cm is drilled along the axis out four linear through-holes with the diameter of 1 mm and the adjacent distance of 3 mm. Four Pt wires of the same diameters as the holes were fixed in the holes, and the end surface of the Pt wires was 1 mm from the end surface of the PTFE block. The 5% Nafion ionomer solution was applied dropwise onto the end surfaces of the Pt wires. After drying, the coating was repeatedly applied until the Nafion polymer solid completely covered the end surfaces of the Pt wires.

Figure 5:
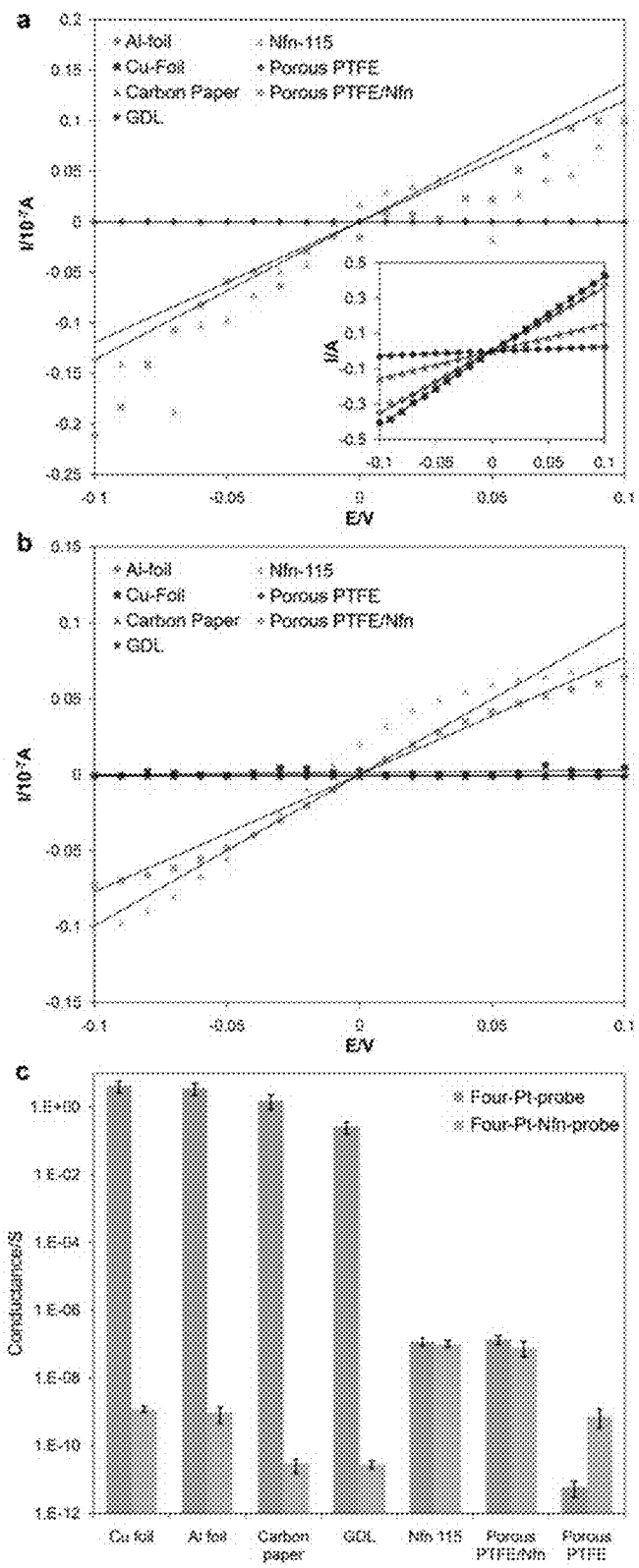
FIG. 5: (a) The test signals for conductivity of different samples by adopting unmodified four-probe method (control example 1 and 2); (b) The test signals for conductivity of different samples by adopting modified four-probe method (example 1 and 2); (c) the results of the conductivity tests of Example 1 and 2 and Control Example 1 and 2.

The middle two Pt wires of the test circuit are connected to the voltage test terminals (reference electrode 1 and 2) of the potentiometer, and the outer two Pt wires are connected to the current test terminal (working electrode and counter electrode).

a. Measurement of Ionic Conductance:

A piece of dry Cu foil, Al foil, carbon paper, gas diffusion layer(GDL), porous PTFE, porous PTFE/Nafion ionomer with a size of 5×5 cm$^2$ is closely contacted with the Nafion ionomer modified end of the test electrode. The potential signals were applied to the voltage test terminals with a voltage range of −1 to 1 V, and the current response signals were then recorded at the current test terminals.

b. Data Processing:

The above measured current data are set as the abscissa, and the voltage data are set as the ordinate, and an approximate linear curve could be obtained as shown in FIG. 5a. The linear fitting of the curve near the zero potential is performed, and the slope d of the fitting curve is the test ion resistance of the sample.

The ionic resistivity of the material is corrected by $\rho = Cd$, and C is the correction factor. When the spacing S between the probes is equal, $$C = 2\pi S$$

The measured ionic conductivity of the samples is shown in FIG. 5c.

Comparative Example 2

The experiment is carried out by the unmodified four-probe method. The cylindrical PTFE block with diameter of 2 cm is drilled along the axis out four linear through-holes with the diameter of 1 mm and the adjacent distance of 3 mm. Four Pt wires of the same diameters as the holes were fixed in the holes, and the end surface of the Pt wires was 0.5 mm reaching out from the end surface of the PTFE block.

The middle two Pt wires of the test circuit are connected to the voltage test terminals (reference electrode 1 and 2) of the potentiometer, and the outer two Pt wires are connected to the current test terminal (working electrode and counter electrode).

a. Measurement of Ionic Conductance:

A piece of dry Cu foil, Al foil, carbon paper, gas diffusion layer(GDL), porous PTFE, porous PTFE/Nafion ionomer with a size of 5×5 cm$^2$ is closely contacted with the Nafion ionomer modified end of the test electrode. The potential signals were applied to the voltage test terminals with a voltage range of −1 to 1 V, and the current response signals were then recorded at the current test terminals.

b. Data Processing:

The above measured current data are set as the abscissa, and the voltage data are set as the ordinate, and an approximate linear curve could be obtained. The linear fitting of the curve near the zero potential is performed, and the slope d of the fitting curve is the test ion resistance of the sample.

The ionic resistivity of the material is corrected by $\rho = Cd$, and C is the correction factor. When the spacing S between the probes is equal, $$C = 2\pi S$$

The measured ionic conductivity of the samples is shown in FIG. 5c. As demonstrated by the results, this measurement effectively blocks the conductance of electrons, while maintains the conductance of ions, which can successfully separate ionic conductance from electronic conductors.

Example 3

The testing instrument is the same as Example 1.

a. Measurement of Ionic Conductance:

A humidified Nafion 115 film with a size of 5×5 cm$^2$ is closely contacted with the Nafion ionomer modified end of the test electrode. The potential signals were applied to the voltage test terminals with a voltage range of −1 to 1 V, and the current response signals were then recorded at the current test terminals.

b. Data Processing:

The above measured current data are set as the abscissa, and the voltage data are set as the ordinate, and an approximate linear curve could be obtained as shown in FIG. 2. The linear fitting of the curve near the zero potential is performed, and the slope d of the fitting curve is the test ion resistance of the sample.

The ionic resistivity of the material is corrected by ρ=Cd, and C is the correction factor. When the spacing S between the probes is equal, $$C=2\pi S$$

The measured ionic conductivity of the humidified Nafion 115 membrane is about 0.128±0.012 S cm$^{-1}$.

Example 4

The testing instrument is the same as Example 1.
a. Measurement of Ionic Conductance:
A carbon paper with a size of 5×5 cm$^2$ is closely contacted with the Nafion ionomer modified end of the test electrode. The potential signals were applied to the voltage test terminals with a voltage range of −1 to 1 V, and the current response signals were then recorded at the current test terminals.
b. Data Processing:
The above measured current data are set as the abscissa, and the voltage data are set as the ordinate, and an approximate linear curve could be obtained as shown in FIG. 2. The linear fitting of the curve near the zero potential is performed, and the slope d of the fitting curve is the test ion resistance of the sample.

The ionic resistivity of the material is corrected by ρ=Cd, and C is the correction factor. When the spacing S between the probes is equal, $$C=2\pi S$$

The measured ionic conductivity of the carbon paper is about 4.17±0.09 mS cm$^{-1}$, which indicates that the influence of the electronic conductance is largely separated.

Example 5

The testing instrument is the same as Example 1.
a. Measurement of Ionic Conductance:
A carbon paper dipped with 5% Nafion ionomer with a size of 5×5 cm$^2$ is closely contacted with the Nafion ionomer modified end of the test electrode. The potential signals were applied to the voltage test terminals with a voltage range of −1 to 1 V, and the current response signals were then recorded at the current test terminals.
b. Data Processing:
The above measured current data are set as the abscissa, and the voltage data are set as the ordinate, and an approximate linear curve could be obtained as shown in FIG. 2. The linear fitting of the curve near the zero potential is performed, and the slope d of the fitting curve is the test ion resistance of the sample.

The ionic resistivity of the material is corrected by ρ=Cd, and C is the correction factor. When the spacing S between the probes is equal, $$C=2\pi S$$

The measured ionic conductivity of the carbon paper is about 20.83±0.56 mS cm$^{-1}$, which indicates the capability of ionic conductance of the materials and eliminates the electronic conductance.

We claim:

1. An ionic conductance measuring device comprises a voltage/current detection part and a test electrode; the test electrode comprises a block of substrate, four linearly arranged through holes on the substrate, four platinum wires inserted in the holes with the upper tips extended outside the block and the opposite tips withdrawn inside the block, the axes of the through holes, as well as the platinum wires, are parallelly aligned in the same plane, the distance between the lower end surface of the platinum wires and the bottom surface of the block substrate is 0.1-2 mm, and the gaps between the bottom ends of the platinum wires and the substrate are filled with the ion conductive polymer.

2. The ionic conductance measuring device of claim 1, wherein the voltage/current testing device is one of a potentiostat, ohmmeter, ammeter, constant voltage power supply, and a constant current meter.

3. The ionic conductance measuring device of claim 1, wherein the distance between the adjacent platinum wires is equal, and the diameters of the platinum wires are equal.

4. The ionic conductance measuring device of claim 1, wherein the substrate material is one of polytetrafluoroethylene, polyether ether ketone and polyethylene.

5. The ionic conductance measuring device of claim 1, wherein the ion conductive polymer is one of perfluorosulfonic acid polymer, sulfonated polyetheretherketone, quaternized polysulfone, and polybenzimidazole.

6. The ionic conductance measuring device of claim 1, wherein the range of the measurement for ionic conductivity is 0.01 to 1000 Ω·cm; the range with minimized error is 0.05 to 100 Ω·cm.

7. The ionic conductance measuring device of claim 1, wherein the testing device also comprises a temperature/humidity controllable test box, which includes three airtight chambers: a dry gas chamber, a wet gas chamber and a testing chamber;
the probes of the voltage/current testing device and the testing electrode are arranged in the testing chamber;
a gas inlet-A and a dry gas outlet are fixed on the dry gas chamber, and the inside of the dry gas chamber is filled with dehydration material; a gas inlet-B and a moist gas outlet are fixed on the wet gas chamber, and the deionized water is contained in chamber; the gas outlets of the dry and wet gas are connected to the testing chamber by tubes, and the inlets are connected to an gas supply source by gas flow meters.

8. The ionic conductance measuring device of claim 7, wherein the dry gas outlet and the wet gas outlet are connected with the test chamber pipeline through the three-way valve, and the three ports of the three-way valve are respectively connected with the testing chamber, the dry gas outlet and the wet gas outlet; the gas flow meters are one of the rotor flow rate meters, electromagnetic flow meters, and differential pressure flow meters.

9. The ionic conductance measuring device of claim 7, wherein the bottom of the test chamber is set with a water outlet, and the water outlet is set with a valve, and the water outlet can be opened or closed, and the water outlet can be opened to discharge liquid water in the test chamber.

10. The ionic conductance measuring device of claim 7, wherein the test chamber is provided with a sample test table, and the sample test table is drilled with several through holes, which can drain the liquid water to the bottom of the testing chamber.

11. The ionic conductance measuring device of claim 7, wherein the humidity controllable testing box is provided with a heat keeping device outside, and the dry gas chamber, wet gas chamber and testing chamber are all covered by the heat keeping device.

12. The ionic conductance measuring device of claim 11, wherein the temperature controlling and keeping device is one of a thermostatic water bath and a electric heating jacket.

13. The ionic conductance measuring device of claim 7, wherein the dry gas chamber, the wet gas chamber and the testing chamber are made of moisture resistant and heat resistant materials, and the moisture resistant and heat resistant material is one of organic glasses, polytetrafluoroethylene and stainless steel.

14. A method for measuring ionic conductivity using the ionic conductance measuring device of claim 1 comprising the followed steps:
   (1) measuring the ionic conductance: a sliced thin piece of the testing sample is tightly pressed on bottom end of the testing electrode block; the second and third platinum wires counted from the left in the test electrode are connected with the potential control terminal, and the first and forth platinum wires counted from the left in the test electrode are connected with the current control terminal; a certain voltage is applied on the voltage testing terminal, and the response current is recorded; the same procedure is repeated at least twice;
   (2) data processing: the measured current is set as the abscissa, and the voltage is set as the ordinate; a plot of current-voltage is obtained, and the linear section near the zero potential part is fitted, and the slope d of the fitted curve is the ionic resistance of the sample to be measured;

the ionic resistivity $\rho$ of the test sample is calculated by $\rho=Cd$, where C is the correction factor and is calculated as follow:

$$C=2\pi/[1/S_1+1/S_2-1/(S_1+S_2)-1/(S_2+S_3)]$$

wherein $S_1$, $S_2$ and $S_3$ are the distance between the first platinum wire and the second platinum wire counted from the left in the test electrode, the second Pt wire and the third Pt wire, the third Pt wire and the fourth Pt wire, respectively; and the conductivity of the sample to be measured is $1/\rho$.

15. The method of claim 14, wherein the applied voltage range in step (1) is −1V to 1V.

16. The method of claim 14, wherein when the length of the test sample on the scale along the line of the connected points of the axes of the platinum wires is more than 10 times of the distance between the Platinum wires, it could be considered to meet the semi-infinite boundary condition, and the conductivity value is calculated directly from the above equation.

17. The method of claim 14, wherein when the ratio of the sample thickness and the distance between the Platinum wires is less than 0.5, a correction curve is required by testing a series of samples to evaluate the relationships between the sample thickness and the testing positions.

18. The method of claim 14, wherein the ionic conductivity test method is used to measure the ionic conductivity of samples as carbon paper, carbon powder, carbon fiber, semiconductor, metal, or polymers.

19. The method of claim 14, wherein the flow rate ratio of the gas inlet A and the gas inlet B is simultaneously introduced, the flow ratio $Q_A:Q_B$ is equal to X:(1−X), where X is the preset humidity, $0\leq X\leq 100\%$; the gas is one of nitrogen, argon, air, and oxygen.

* * * * *